(12) United States Patent
Ryhänen et al.

(10) Patent No.: US 8,148,686 B2
(45) Date of Patent: Apr. 3, 2012

(54) SENSING ARRANGEMENT

(75) Inventors: Tapani Ryhänen, Helsinki (FI); Kari Hjelt, Espoo (FI)

(73) Assignee: Nokia Corporation, Espoo (FI)

( * ) Notice: Subject to any disclaimer, the term of this patent is extended or adjusted under 35 U.S.C. 154(b) by 0 days.

(21) Appl. No.: 12/899,701

(22) Filed: Oct. 7, 2010

(65) Prior Publication Data

US 2011/0019373 A1  Jan. 27, 2011

Related U.S. Application Data

(63) Continuation of application No. 10/763,805, filed on Jan. 22, 2004, now Pat. No. 7,813,534.

(30) Foreign Application Priority Data

Jan. 22, 2003 (FI) ..................................... 20030101

(51) Int. Cl.
 *G02F 1/01* (2006.01)
(52) U.S. Cl. .......................... 250/330; 713/182; 713/186
(58) Field of Classification Search .................. 250/330; 713/182, 186
 See application file for complete search history.

(56) References Cited

U.S. PATENT DOCUMENTS

| | | |
|---|---|---|
| 4,577,345 A | 3/1986 | Abramov |
| 5,327,162 A | 7/1994 | Soma |
| 5,631,453 A | 5/1997 | Maeda |
| 5,862,248 A | 1/1999 | Salatino et al. |
| 5,887,343 A | 3/1999 | Salatino et al. |
| 5,956,415 A | 9/1999 | McCalley et al. |
| 5,959,457 A | 9/1999 | Berberich |
| 6,055,324 A | 4/2000 | Fujieda |
| 6,067,368 A | 5/2000 | Setlak et al. |
| 6,073,343 A | 6/2000 | Petrick et al. |
| 6,088,585 A | 7/2000 | Schmitt et al. |
| 6,175,232 B1 | 1/2001 | Decoulon et al. |
| 6,181,958 B1 | 1/2001 | Steuer et al. |
| 6,289,114 B1 | 9/2001 | Mainguet |
| 6,327,376 B1 | 12/2001 | Harkin |
| 6,347,040 B1 | 2/2002 | Fries et al. |

(Continued)

FOREIGN PATENT DOCUMENTS

EP  0789334  8/1997

(Continued)

OTHER PUBLICATIONS

English Abstract of Japanese Publication No. JP 2001-510579, published Jul. 31, 2007 (1 page).

(Continued)

*Primary Examiner* — David Porta
*Assistant Examiner* — Hugh H Maupin

(57) ABSTRACT

The invention relates to an arrangement for sensing ambient conditions in electric equipment. These conditions may include verification of the user, the location of the equipment and various properties of the environment. The invention is preferably applied in mobile terminals. One idea of the invention is to provide a sensor arrangement with a substrate (663) that forms at least part of a sensor, and also serves as a substrate for other sensors (695-698). The substrate is preferably flexible so that it can be formed in a shape which is follows the shape of the device cover. The invention also describes a way to create two- or three-dimensional electrode structures that can be used to optimize the performance of the sensor. When the surface structure is designed to follow the shape of a finger, a very small pressure is required when sliding the finger along the sensor surface. This way the use of the sensor is ergonomic and the measurement is made very reliable.

19 Claims, 11 Drawing Sheets

U.S. PATENT DOCUMENTS

| | | |
|---|---|---|
| 6,528,740 B2 | 3/2003 | Miyoshi |
| 6,608,263 B2 | 8/2003 | Myojin |
| 6,643,389 B1 | 11/2003 | Raynal et al. |
| 6,657,141 B1 | 12/2003 | Myojin |
| 6,689,967 B2 | 2/2004 | Myojin |
| 6,700,565 B2 | 3/2004 | Niiyama |
| 6,714,666 B1 | 3/2004 | Morimura et al. |
| 6,829,950 B2 | 12/2004 | Ganapathi et al. |
| 7,099,496 B2 | 8/2006 | Benkley, III |
| 7,251,351 B2 | 7/2007 | Mathiassen et al. |
| 7,848,550 B2 | 12/2010 | Mathiassen et al. |
| 2002/0014651 A1 | 2/2002 | Thomas |
| 2003/0210809 A1 | 11/2003 | Kim |

FOREIGN PATENT DOCUMENTS

| | | |
|---|---|---|
| EP | 0791899 | 8/1997 |
| EP | 1073117 | 1/2011 |
| JP | 06104641 | 4/1994 |
| JP | 8305815 | 11/1996 |
| JP | 09231346 | 9/1997 |
| JP | 09289268 | 11/1997 |
| JP | 2000262494 | 9/2000 |
| JP | 2001184490 | 7/2001 |
| JP | 2001510579 | 7/2001 |
| JP | 2001324303 | 11/2001 |
| JP | 2002501803 | 1/2002 |
| JP | 2002245443 | 8/2002 |
| JP | 2002298130 | 10/2002 |
| JP | 200316433 | 1/2003 |
| JP | 2003536085 | 12/2003 |
| WO | 9939631 | 8/1999 |
| WO | 0106448 | 1/2001 |
| WO | 0199035 | 12/2001 |
| WO | 0199036 | 12/2001 |
| WO | 0247018 | 6/2002 |
| WO | 03075210 | 9/2003 |

OTHER PUBLICATIONS

Patent Abstracts of Japan, Japanese Publication No. JP 09-231346, McCalley et al., published May 9, 1997 (1 page).

Patent Abstracts of Japan, Japanese Publication No. JP 09-289268, Salatino et al., published Nov. 4, 1997 (1 page).

English Abstract of Japanese Publication No. JP 2002-501803, published Jan. 22, 2002 (1 page).

English Abstract of Japanese Publication No. JP-8305815, Ikegawa Toshio, published Nov. 22, 1996 (1 page).

Patent Abstracts of Japan, Japanese Publication No. JP 2001-324303, Morimura Hiroki et al., published Nov. 22, 2001 (1 page).

Patent Abstracts of Japan, Japanese Publication No. JP 2002-298130, Yamaguchi Tsutomu et al., published Oct. 11, 2002 (1 page).

Patent Abstracts of Japan, Japanese Publication No. JP 2000-262494, Funakoshi Seichi et al., published Sep. 26, 2000 (1 page).

Patent Abstracts of Japan, Japanese Publication No. JP 2002-245443, Fujieda Ichiro, published Aug. 30, 2002 (1 page).

Machine Translation of Japanese Publication JP 06-104641, Watanabe Takaya, published Apr. 15, 1995 (5 pages) plus English Abstract of same (1 page).

English Abstract of JP Publication No. JP 2001-184490, Horinouchi Teruhiko, published Jul. 6, 2011 (1 page).

English Abstract of JP Publication No. JP 2003-16433, Mizuko Yoichi, published Jan. 17, 2003 (1 page).

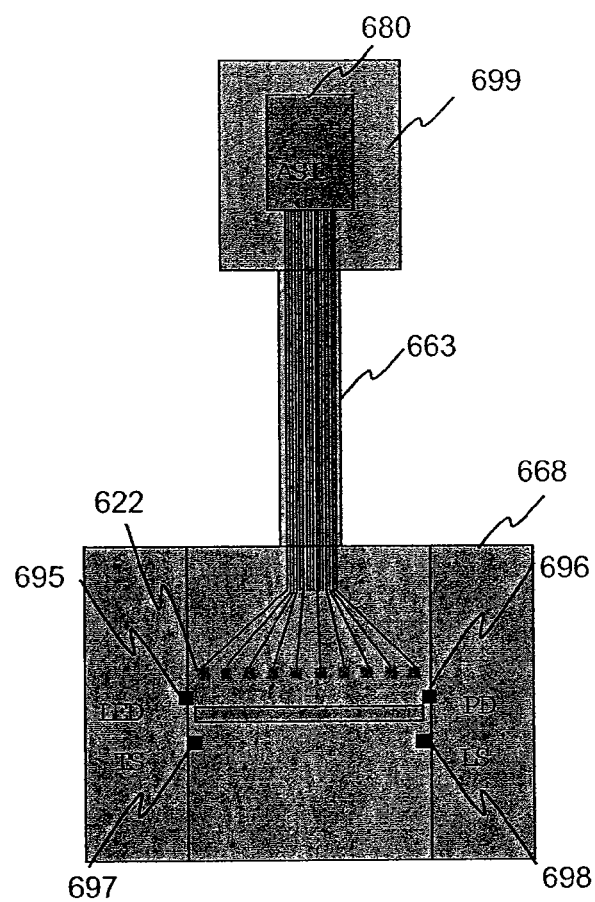
FIG. 6 a
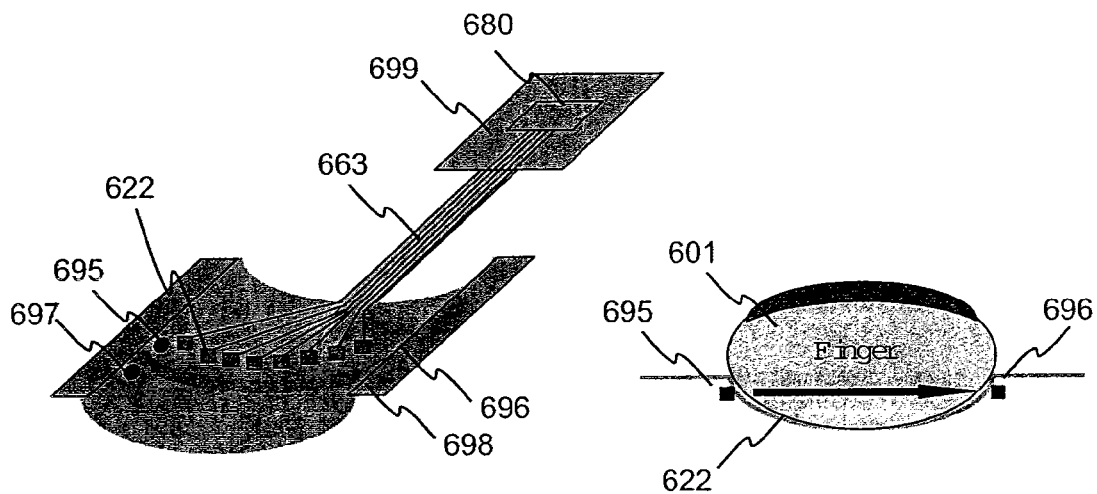
FIG. 6 b                                   FIG. 6 c

11

12

13

14

15

SENSING ARRANGEMENT

CROSS-REFERENCE TO RELATED APPLICATIONS

This application is a continuation of U.S. application Ser. No. 10/763,805 filed Jan. 22, 2004 now U.S. Pat. No. 7,813,534 which claims priority from Finnish Application No. 20030101 filed Jan. 22, 2003.

TECHNICAL FIELD OF THE INVENTION

The invention relates to an arrangement for sensing ambient conditions in electric equipment and/or for sensing biometric variables of a user. These conditions may include verification of the user, the location of the equipment and various properties of the environment. The invention is preferably applied in mobile terminals.

BACKGROUND ART OF THE INVENTION

There is a need of providing sensors in mobile terminals in order to make the mobile terminal capable of sensing its ambient conditions. There is also a need for fingerprint sensors and other biometric sensors that can be used for authenticating the user of the terminal and for measuring other biometric variables from the user. The information can be used for context awareness applications where the ambient information and/or the user information is used e.g. for controlling the user interface profile and different settings of the mobile terminal user interface. The present invention relates to general sensing arrangements, but the prior art is next described using a fingerprint sensor first as an example.

For example, there exist several kinds of fingerprint sensors: skin impedance based sensor, thermal sensors, and optical sensors. The most practical solution for authentication of a user of small appliances, such as mobile terminals, is based on capacitive impedance measurement. The basic idea of the capacitive fingerprint sensor to measure the change of skin impedance is described in FIGS. 1A and 1B. An array of sensors 120 measure the skin impedance values when a finger 101 is gradually pulled over the array of sensors. The capacitance between the electrode surface and the conductive saline layer inside the skin surface varies as a function of distance to the conductive layer. The varying air gap and the dead horny cells in the surface of the skin form the capacitance 125 to the conductive layers 121, 122 forming the electrodes of the capacitive sensor.

FIG. 2 shows another example including a rough equivalent circuit of the skin impedance and the impedance measurement principle. Skin has a fixed resistive tissue component 202, and a fixed resistive surface component 203. The measurement capacitance also has a fixed component 272 and a component 271 that varies according to the surface form of the finger. The capacitive fingerprint sensor measures the varying capacitive component by applying an alternating voltage 281 to a drive electrode 222 and measuring a signal from a sensor electrode 221. The signal is amplified with a low noise amplifier 282, and the phase difference between driver and sensing electrodes is measured, 283. Interference can be suppressed with a guard electrode, which is kept in the same potential as the signal input using a buffer 285.

A fingerprint sensor and most other sensors also require a signal processing circuit, which is preferably a silicon-based integrated circuit. One solution for providing a fingerprint sensor would be to use an integrated circuit, which would serve both as capacitive measurement electrodes and as signal processing electronics. This integrated circuit would then be mounted on the surface of the appliance. However, the area needed for capturing the capacitive image of the fingerprint is roughly on the scale of one square centimeter. This is a very large area for using a silicon integrated circuit as measurement electrodes. Furthermore, the measurement consists of hundreds of capacitive pixels that are arranged in a row or in a matrix depending on the measurement principle. A lot of wiring is needed and the measurement electrodes need to be isolated from the integrated circuits. Therefore a cost efficient method for connecting the capacitive electrodes to the signal processing silicon integrated circuit is needed.

One typical prior art solution is described in patent documents U.S. Pat. No. 5,887,343 and U.S. Pat. No. 6,067,368. The problem is solved by using a separate insulating planar substrate to form the measurement electrode. This substrate contains the interconnecting wiring and the vias through the substrate. The substrate is connected to the silicon integrated circuit containing the signal and data processing capabilities. However, this solution is complicated to manufacture because a large number of interconnecting wiring must be connected within a small space. Such wiring also is not very robust, which tends to make the structure to break easily in mobile use.

Another prior art solution is to create the measurement electrodes directly on top of the silicon wafer. This leads to a simple configuration of interconnecting wiring but the solution requires a large silicon surface due to the large area needed for the electrodes.

One disadvantage with the prior art solutions relates to the ergonomics of the sensor. A finger must be pressed rather heavily against the flat sensor in order to achieve sufficient contact area between the sensor and the finger. Therefore the measurement may often fail when the finger is not pressed and slid properly along the sensor surface.

Another problem with fingerprint sensors is the easy manufacturing of an artificial finger for user identity falsification. The prior art fingerprint sensors cannot reliably distinguish living tissue finger from an artificial plastic replica.

A further problem of the prior art solutions relates to the positioning of various sensors. In order to sense the ambient conditions the sensors need to have an interaction with the environment outside the equipment. Therefore the sensors should be located on the cover of the equipment. Sensors of this kind are generally fixed to the main printed wired board (pwb) of the equipment, and the sensors are made to extend to the surface of the equipment housing through holes in the cover. However, the surfaces of the modern equipment, such as mobile terminals, tend to have designs with three-dimensional curvature. Therefore the distance between the pwb and the cover surface varies which makes designing the sensor structure difficult. The sensors should also have determined locations on the surface of the equipment cover, and it may be difficult to design the layout of the main pwb so that the determined sensor locations are achieved. One solution to this problem is to fix the sensors to the equipment cover, but then the attachment of the sensors to the cover as well as arranging the wiring between the sensors and the main printed wired board would be difficult to realize in mass production.

SUMMARY OF THE INVENTION

The purpose of the invention is to provide a sensing arrangement with improvements related to the aforementioned disadvantages. The invented arrangement for sensors facilitates good security properties and ergonomics, as well as good suitability to serial production. Hence, the invention presents a substantial improvement to the cost efficiency and reliability of the sensors, especially in mobile applications.

A sensor arrangement comprising at least one sensor, at least one integrated signal processing circuit for the measurement of signals from the at least one sensor, and interconnecting wiring between the at least one sensor and the integrated circuit, is characterized in that the arrangement comprises a substrate, said substrate forming at least part of said interconnecting wiring and said substrate is further arranged to serve as a functional part of at least one said sensor.

The invention also concerns a mobile terminal, which comprises a sensor arrangement according to the invention.

One preferred embodiment of the invention comprises at least sensor, electrodes and the integrated circuit on a flexible substrate. Such an arrangement can be e.g. molded in the cover of a mobile station.

Further preferred embodiments of the invention are described in more detail below.

One idea of the invention is to provide a sensor arrangement with a substrate that forms at least part of a sensor, and preferably also serves as a substrate for other sensors. The substrate is preferably flexible so that it can be formed in a shape, which follows the shape of the device cover. The invention also describes a way to create two- or three-dimensional forms for the electrode structures that can be used to optimize the performance of the sensor. When the two- or three-dimensional surface structure is designed to follow the shape of a finger, a very small pressure is required when sliding the finger along the sensor surface. This way the use of the sensor is ergonomic and the measurement is made very reliable.

The invention also facilitates the realization of a multi sensor microsystem. The sensor elements and the measurement electronics such as ASICs can be integrated into three-dimensional module using chip-on-flex (COF) technology.

The COF technology is based on the use of flexible Kapton.® film, for example, as the substrate for wiring and attachment of sensor and ASIC chips. The ICs and sensors can be protected using molded polymer cover on top. The flexible circuit board (e.g. Kapton.® film) enables the creation of 2D or 3D structures so that part of the sensors and electronics can be placed in the vicinity of the device cover.

The possibility to manufacture a curved surface in the fingerprint sensor makes it possible to integrate an optical detection of blood circulation by light absorption. This way it is possible to verify that the finger belongs to a living human being.

It is also possible to integrate other types of sensors to the sensor unit. For example, in one embodiment of the invention a light emitting diode and a light sensitive detector are placed on the opposite sides of the finger groove in order to measure light absorption through the finger. The wavelength of the light used is such that blood in a live finger causes maximal absorption signal. This way oxidized hemoglobin can be detected from the user's finger. Thus by this method also the heartbeat rate can be monitored. This makes the usage of any artificial fingers for identification falsification very difficult. In addition, other sensors such as temperature TS and light LS sensors can be integrated within the finger groove and embedded into the fingerprint sensor package. In general, using a flexible film as a substrate gives flexibility in placing of the sensors in required locations. The flexible film can, for example, follow the shape of a device cover.

A further idea of the invention is an inductively tuned capacitive sensor that can be integrated in the cover of e.g. a mobile phone. The tuned capacitor sensor is shown to be highly sensitive for resistive losses that result from resistive material in contact with the capacitor electrodes. Based on the impedance measurement, the drop of the Q value of the tuned sensor indicates the contacting material: galvanic contact to the sensor electrodes is not needed. The inductive coupling can be done to several tuned sensors at the same or different resonance frequencies, or the coupling can be modulated from the sensor side. Use of different resonance frequencies enables the distinguishing between different sensor elements. While the inductively tuned capacitive sensors can be coupled inductively to the multi chip module containing the measurement electronics, the additional wiring in the assembly phase is not needed. This way it is possible to provide a totally sealed, waterproof device.

The fabrication process of the invention is suitable for mass production, and the invention can be applied to existing sensor measurement concepts and electronics to make the fabrication of the device more cost efficient.

BRIEF DESCRIPTION OF THE DRAWINGS

Next the invention will be described in greater detail with reference to exemplary embodiments in accordance with the accompanying drawings, in which FIG. 6a illustrates a top view of an exemplary arrangement according to the invention, in which there is fingerprint sensor, optical sensor and other sensors applied on a flexible substrate, FIG. 6b illustrates a perspective view of an exemplary arrangement according to the invention, in which there are fingerprint, optical and other sensors applied on a flexible substrate, FIG. 6c illustrates a cross sectional view of an exemplary arrangement according to the invention, in which there is fingerprint, optical and other sensors applied on a flexible substrate.

DETAILED DESCRIPTION

Figure 1A:
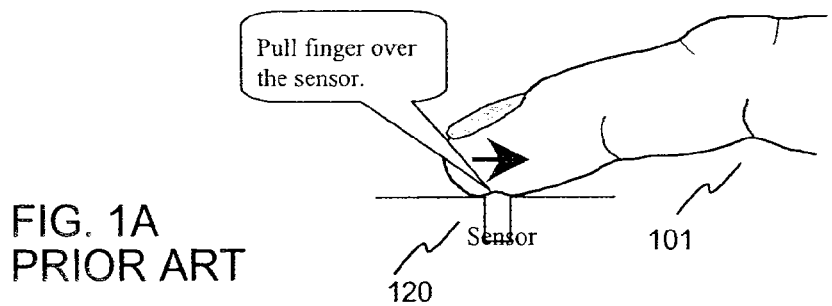
FIG. 1A illustrates using a capacitive fingerprint sensor.
Figure 1B:
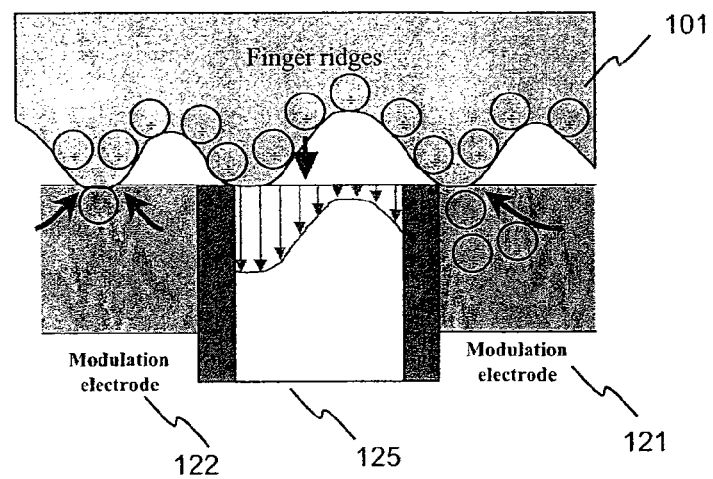
FIG. 1B illustrates the operating principle of a prior art capacitive fingerprint sensor.
Figure 2:
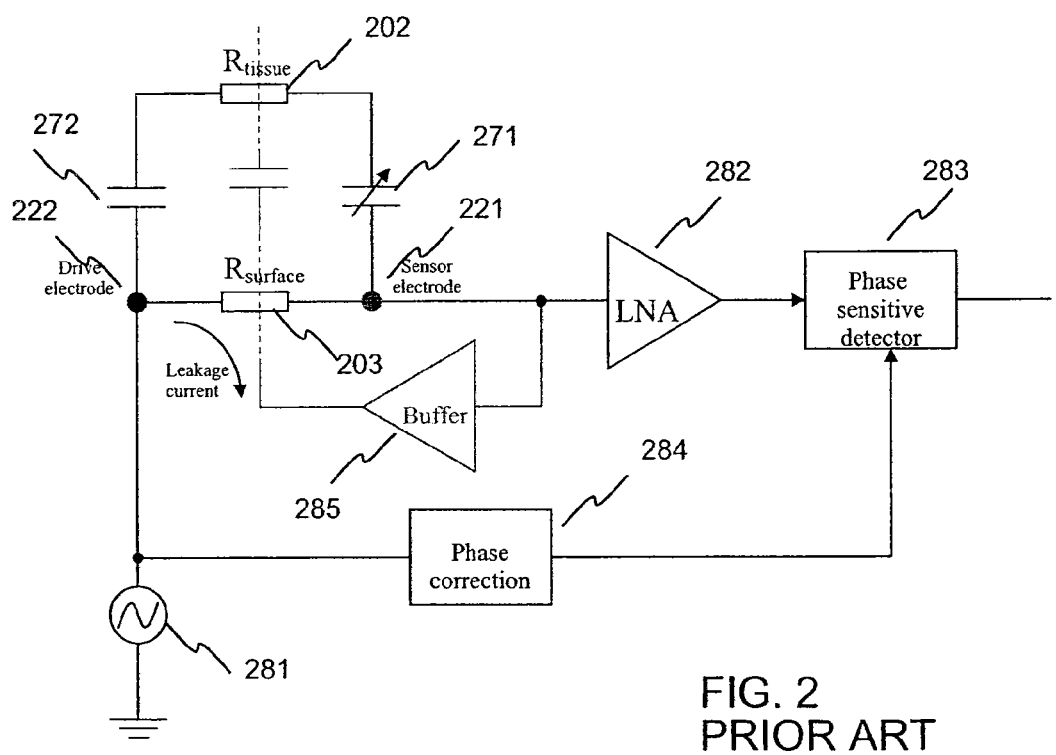
FIG. 2 illustrates a block diagram describing the measurement of skin impedance using active guarding.

FIGS. 1A, 1B and 2 were explained above in the description of prior art.

Figure 3:
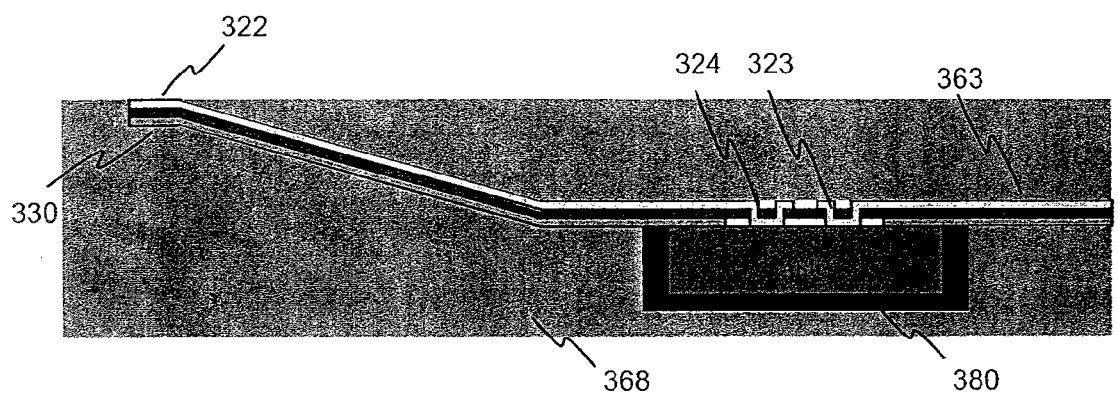
FIG. 3 illustrates a cross section of an exemplary arrangement according to the invention, in which a flexible substrate is applied to serve as a surface for electrodes and electrical connections of the unit.

FIG. 3 illustrates an embodiment of the invention enabling a two- or three-dimensional form of the electrode-finger interface. One end of a flexible printed, wired substrate is used for electrodes 322, and other part of the substrate 363 is used for external connection. FIG. 3 also shows the connections between the metallized surfaces of the flexible substrate and the ASIC 380. The wiring to the electrodes 322 and guard 330 is provided using two-sided metallization of the flex film and vias 323, 324. This arrangement including the flexible substrate, sensor and ASIC can be directly molded into a cover 368 of, e.g., a mobile phone.

Figure 4:
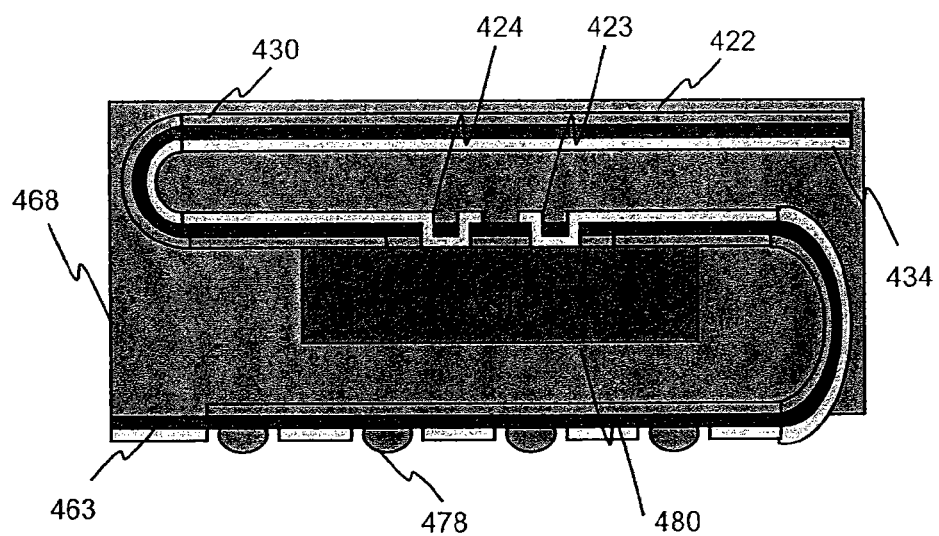
FIG. 4 illustrates a cross section of an exemplary arrangement according to the invention, in which a flexible substrate is bent to serve as electrodes and a surface for electrical connections of the unit.

FIG. 4 illustrates an embodiment of inventive arrangement where the connection to other electronics is made by bending a flexible printed wired board (PWB) or film substrate 463 to under the unit, and attaching soldering balls 478 to the flex. In this embodiment the other end of the flex is bent above the unit in order to use the end of the flex as electrodes. The connections 423, 424 to the ASIC 480 can be made similar to the embodiment of FIG. 3. On the electrode end of the flex one metallized surface 430 serves as sensing electrode and the second metallized surface 434 of the flex serves as a guard electrode. The arrangement can be molded into plastic 468 to form an integral component.

Figure 5:
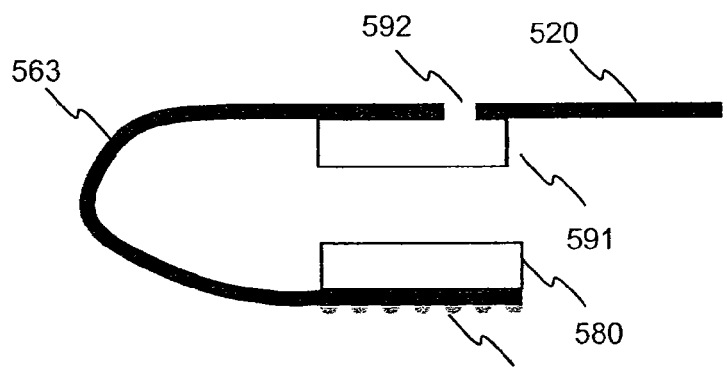
FIG. 5 illustrates a cross section of an exemplary arrangement according to the invention, in which there are additional sensors applied on a flexible substrate.

FIG. 5 illustrates an embodiment of inventive arrangement where there is a set 591 of other sensors on the flexible substrate 563 in addition to fingerprint sensor electrodes 520. The sensors may include optical sensors, a temperature sensor, a humidity sensor, a pressure sensor, an acceleration sensor, alignment sensor, biometric sensors etc. There is an aperture 592 in the flexible substrate for providing a sensing interface between outer part of the device and the sensors. The other end of the flexible substrate 563 comprises the ASIC circuit 580 and electrical connection 578 to the external circuits.

FIGS. 6a, 6b and 6c illustrate an exemplary arrangement according to the invention, in which there are fingerprint, optical and other sensors applied on a flexible substrate. FIG. 6a shows a top view, FIG. 6b shows a perspective view and FIG. 6c shows a cross-section view of the arrangement. The ASIC 680 is mounted on a printed wired board 699, which may be a board used for other electronics of the device. The ASIC is connected to a flexible substrate 663, which connects the ASIC to the sensors and electrodes. The sensor substrate 668 can also be made of the flexible substrate. The substrate is of a curved form in order to provide a suitable surface for a finger 601. There are in this exemplary arrangement eight electrodes 622 provided on the flexible substrate for the fingerprint sensor. An optical pulse oximeter sensor is formed with an infrared LED 695 and a photodiode 696. Infrared pulsed light provided by the LED is measured with the photodiode after the beam has penetrated through the finger 601. This way it is possible to verify that the finger includes blood, the concentration of which fluctuates according to the heart pulse. The arrangement also comprises a temperature sensor 697 that can be used for measuring the ambient temperature or the temperature of the finger. The arrangement may also comprise a light sensor 698 for measuring the ambient light. This information can be used e.g. for controlling the intensity of the display of the device. The arrangement can further comprise a humidity sensor for measuring the ambient humidity.

Instead of or in addition to providing a fingerprint sensor it may be advantageous to provide one or several skin contact sensors. A skin contact sensor can be used e.g. for checking whether the device is held in hand, or whether a mobile station contacts the ear of the user (i.e. the mobile station is used for a phone conversation).

Figure 7A:
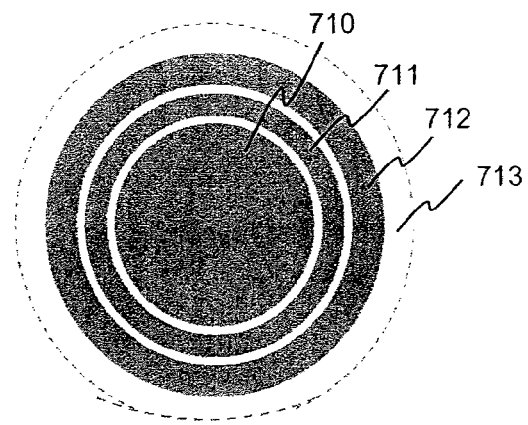
FIG. 7a illustrates a top view of an exemplary contact electrode for an arrangement according to the invention.
Figure 7B:
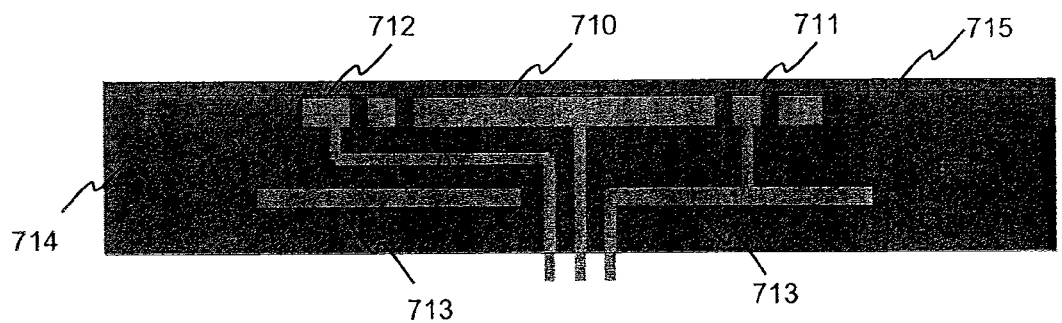
FIG. 7b illustrates a cross sectional view of an exemplary contact electrode for an arrangement according to the invention.

FIGS. 7a and 7b illustrate an example of a skin contact electrode. FIG. 7a shows a top view of the electrodes and FIG. 7b shows a cross section view of the electrodes and their wiring. The skin contact is determined by measuring the impedance between the center electrode 710 and the electrode 712 forming the outer ring. The electrode 711 serves as a guard ring. The guard electrode also forms a guard disc 713 below the active electrodes 710 and 712. The electrodes can be molded into plastic 714, thus e.g. forming a separate component or being integrated into a device cover. There is also a thin passivation layer 715 on the surface of the cover.

Figure 7C:
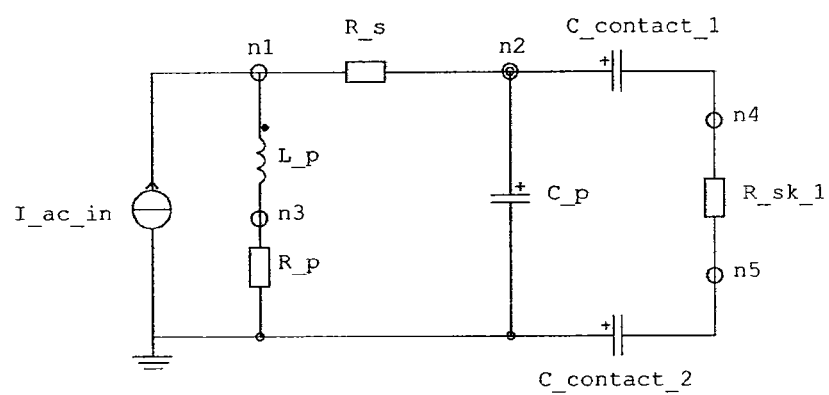
FIG. 7c illustrates an equivalent circuit for a contact measurement with the exemplary contact electrode according to FIGS. 7a and 7b.

FIG. 7c illustrates an equivalent circuit for a skin contact measurement with the exemplary contact electrode according to FIGS. 7a and 7b. The actual skin impedance R_sk_1 is measured by applying an alternating current I_ac_in to the center and outer electrodes. Contact capacitances C_contact_1 and C_contact_2 appear in series with the skin impedance. The measured voltage in point n3 is also affected by the resistance of the electrode wires R s, as well as by inductive component L_p, resistive component R_p and capacitive component C_p of the substrate effect.

Figure 8:
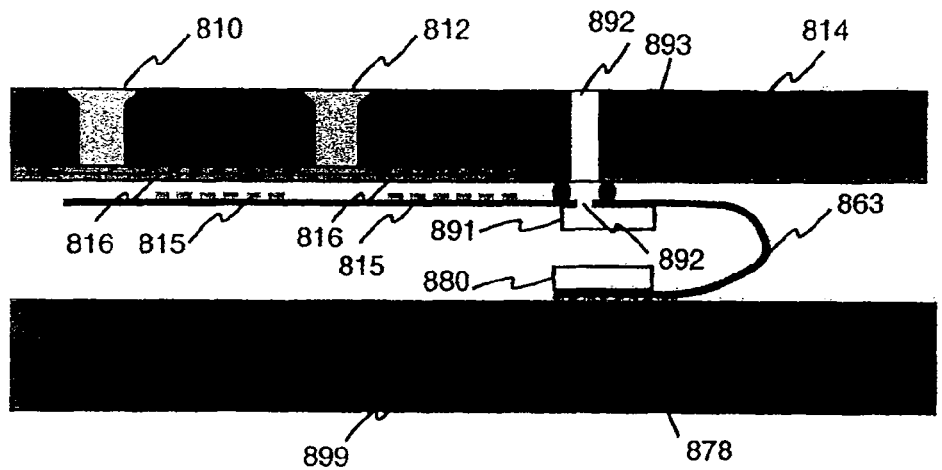
FIG. 8 illustrates a cross sectional view of an exemplary arrangement according to the invention, in which there is an inductive skin contact sensor together with optical and other sensors applied using a flexible substrate.

FIG. 8 illustrates a cross section view of an exemplary arrangement according to the invention, in which there is an inductive skin contact sensor together with optical and other sensors applied using a flexible substrate. The skin contact is measured by applying an alternating current to conductive electrodes 810 and 812, which can be made e.g. of conductive polymer. The electrodes are connected to ends of a planar coil 816, which receives inductive energy from another coil 815. The coil 815 is located on a flexible substrate 863, which can be on a small distance from the device cover 814. Other sensors are installed in a sensor box 891 on the flexible substrate. There is an aperture 892 through the substrate and the device cover for providing a sensing interface between the sensors and the ambient of the device. There is a gasket 893 between the flexible substrate and the device cover sealing the aperture from the inner volume of the device. The flexible substrate is further connected to an ASIC circuit 880, which provides the measurement electronics and circuits for processing the measured data. The flexible substrate provides wiring between the sensors and the ASIC. The ASIC and the substrate are further connected 878 to a printed wired board 899 of the device.

Figure 9A:
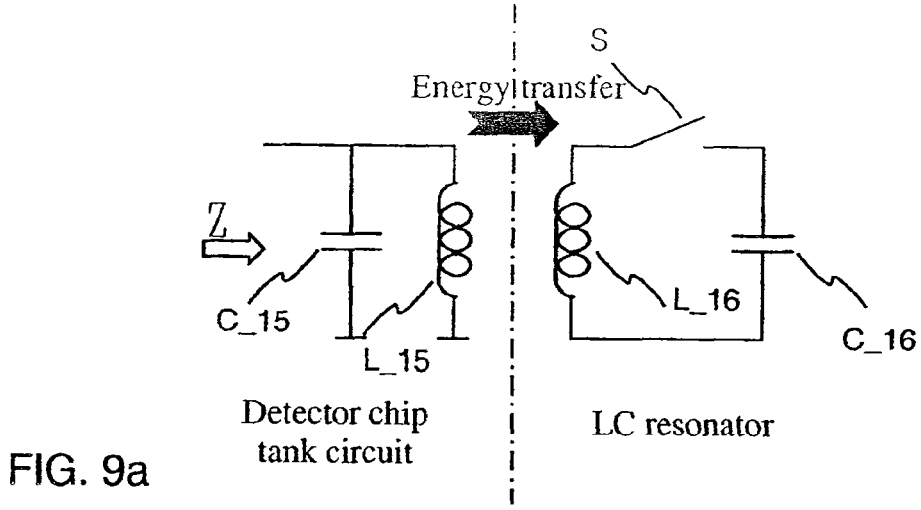
FIG. 9a illustrates a circuit of a first embodiment for inductive contact measurement.
Figure 9B:
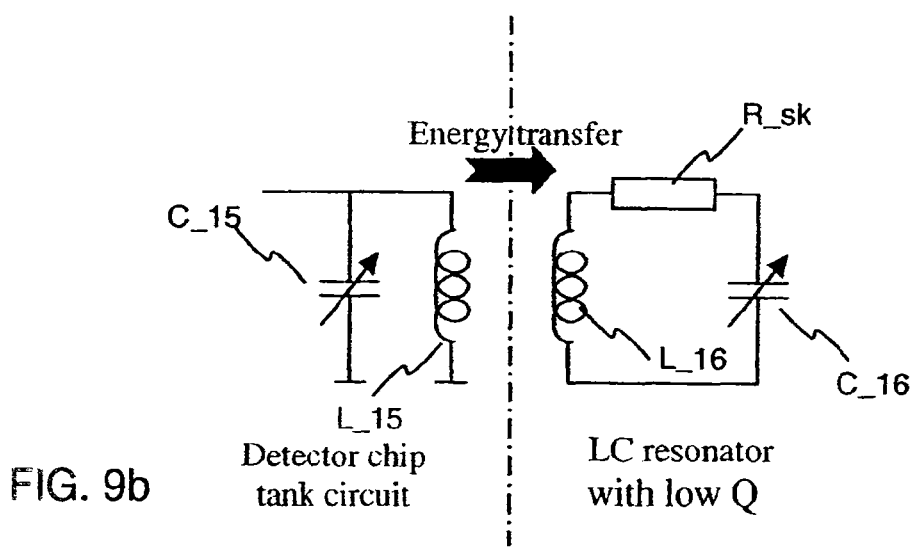
FIG. 9b illustrates a circuit of a second embodiment for inductive contact measurement.

FIGS. 9a and 9b illustrate two basic principles of the inductive measurement of skin contact. In FIG. 9a the circuit has fixed capacitances and thus fixed resonance frequency. The skin contact has thus an on/off switching effect to the resonance circuit. In FIG. 9b the circuit has variable capacitors and low Q value so that the resonance frequency can be changed according to the effect of the skin contact. This circuit gives more accurate information on the skin contact effect, but on the other hand the complexity and energy consumption are higher. FIGS. 9a and 9b show circuits where the sensor side is a passive LC resonator. However, it is also possible to use an active measurement circuit, as shown in FIG. 1b.

Figure 10:
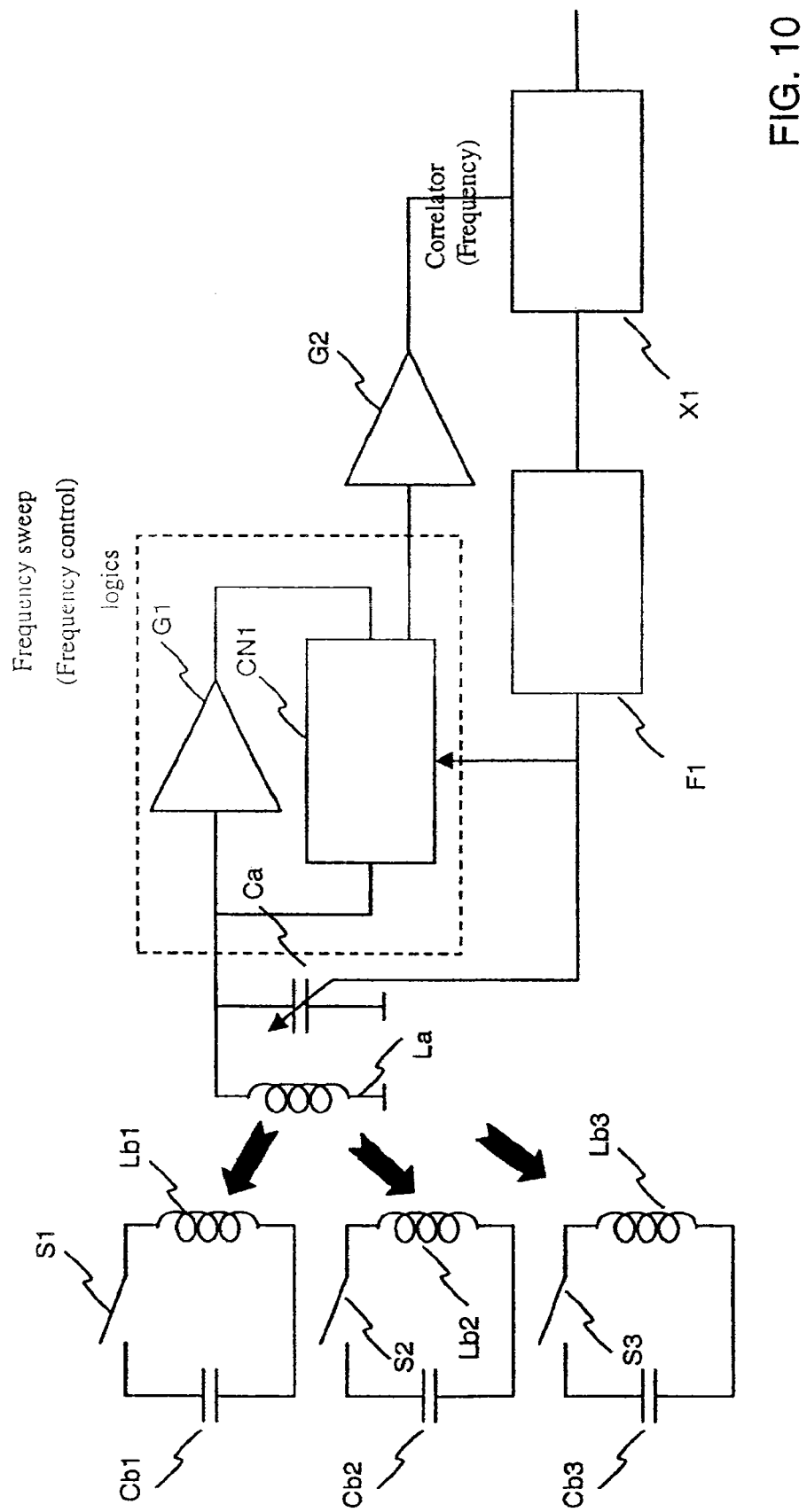
FIG. 10 illustrates a circuit of an exemplary multi-channel inductive measurement with sensors for measuring several sensors.

FIG. 10 illustrates an arrangement with inductive sensor coupling, which comprises circuits for measuring several sensors using different measurement frequencies. The arrangement has three sensor circuits each forming a resonance circuit; Cb1-Lb1-S1, Cb2-Lb2-S2 and Cb3-Lb3-S3. The primary resonance circuit La-Ca can be adjusted to different frequencies by controlling capacitance Ca. A Frequency sweep logics F1 controls both the resonance frequency and frequency of a self-oscillating system that comprises an amplifier G1 and a control block CN1. The frequency is swept within a frequency range that covers resonance frequencies of each sensor. With a correlator it is then possible to define which sensors are resonating on their individual resonance frequencies, or to define the exact resonance frequency for each sensor circuit.

Figure 11A:
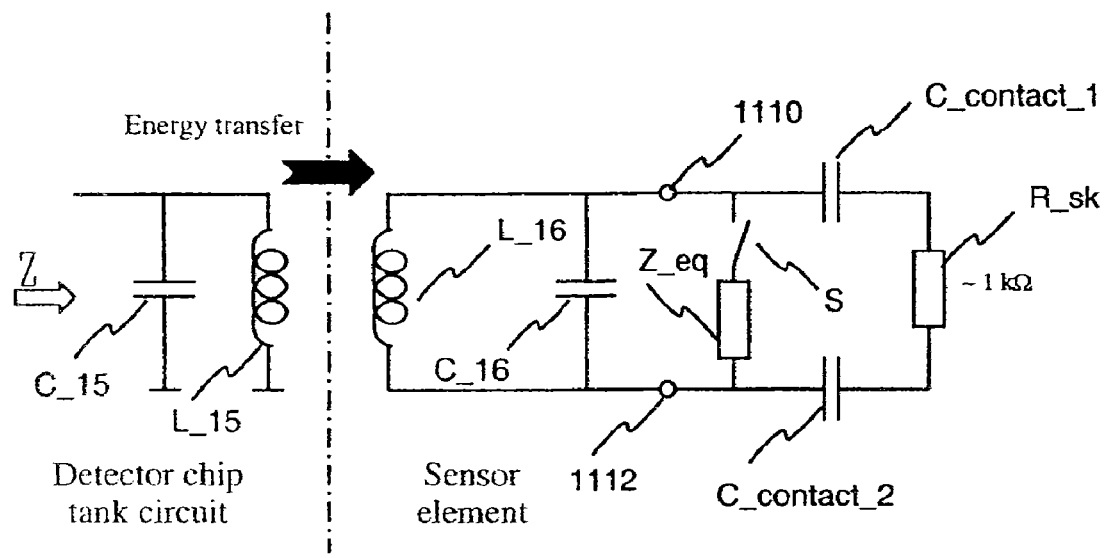
FIG. 11a illustrates an exemplary circuit for passive inductive contact measurement according to the invention.

FIG. 11a illustrates an equivalent circuit for a skin contact measurement with a passive inductive arrangement. The actual skin impedance R_sk is measured by applying an alternating current to the primary coil L_15, C_15 and measuring the impedance Z. Due to energy transfer between coils a measurement current is induced to the secondary coil L_16, C_16. The secondary impedance is affected by the actual skin resistance R_sk and contact capacitances C_contact_1 and C_contact_2 appearing at the skin-electrode contact. The value of the skin resistance R_sk is typically one kilo-ohm. When skin comes into contact with the electrodes, the effect is the same as connecting with a switch S an impedance Z_eq in parallel with the secondary coil. The value of Z_eq is determined by the skin resistance and the contact capacitances, and its value is typically e.g. 200 kilo-ohms. The change in the secondary impedance can then be detected by measuring the primary impedance Z.

Figure 11B:
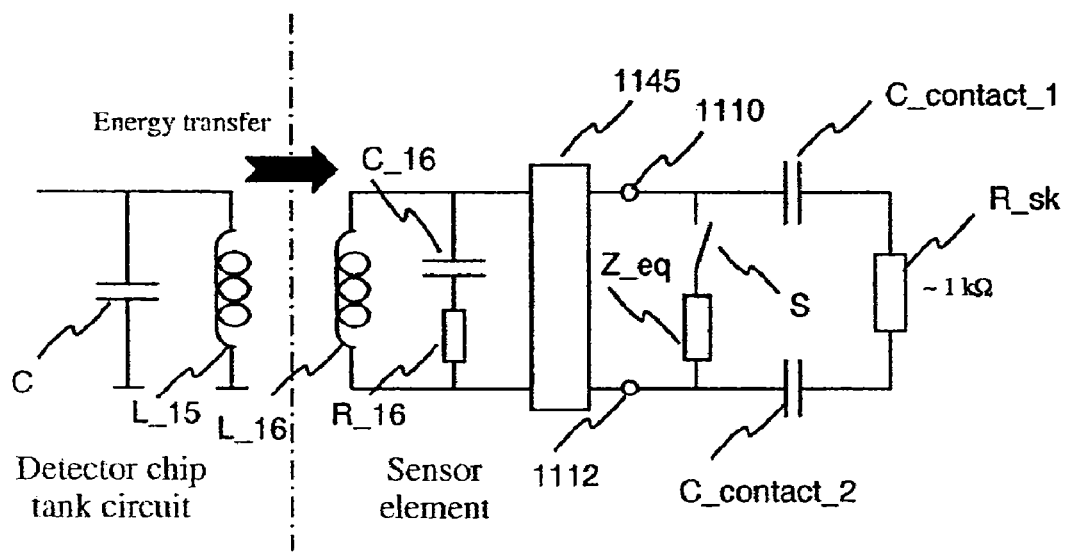
FIG. 11b illustrates an exemplary circuit for active inductive contact measurement according to the invention.

FIG. 11b illustrates an equivalent circuit for a skin contact measurement with an active inductive arrangement. In this arrangement there is an active measurement circuit 1145, which receives its operating power by inductive coupling from the tank circuit. The circuit 1145 measures the impedance between points 1110 and 1112, and transfers the measurement values by modulating the inductive coupling. The modulation may change the impedance measured from the detector side, or the modulation may change the frequency with which the tank circuit oscillates. In order to vary the frequency, the circuits C-L_15 and L_16-C_16 are designed to oscillate within a wide frequency band. It is also possible to use one circuit 1145 for measuring several sensors. The measurement values from each sensor can be transferred sequentially to the detector with the modulation.

In previous Figures the idea of inductive coupling has been explained as applied to skin contact measurement. However, the inventive idea of inductive measurement is not in any way restricted to the implementations of skin contact measurement; the inductive arrangement can be used for applying energy to any type of sensors, and for measuring the sensor's output. The inventive idea of inductive measurement is not either restricted only for use with the inventive sensor arrangement including a substrate. The inductive coupling gives a possibility to provide a totally sealed cover structure without any sensor wiring between the sensors on the cover and inner electronics.

In the following some solutions are presented for providing shielding/guarding for the electrodes in an arrangement according to the invention. These examples are related to fingerprint sensors, but the solutions can also be used in, e.g., skin contact measurements.

Figure 12:
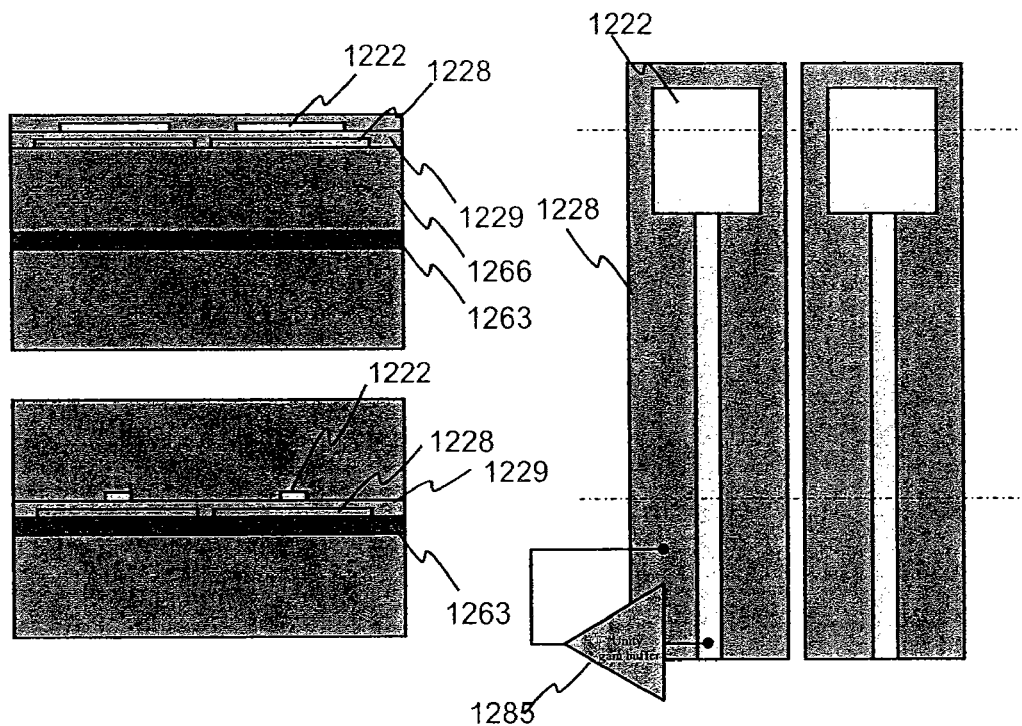
FIG. 12 illustrates guarding in an exemplary arrangement according to the invention

FIG. 12 illustrates top and cross-section views of exemplary sensing electrodes 1222 and guard electrodes 1228 on a substrate 1263. The guard electrodes 1228 are located under the sensing electrodes 1222 with an insulating layer 1229 between the electrodes. In this embodiment the guard electrodes have larger surface. A buffer amplifier 1285 keeps the guard electrodes in the same potential as the sensor electrodes and thus the sensor electrodes are less loaded by adjacent materials or interference. FIG. 12 also shows material 1266, e.g., plastic, wherein the sensor is molded.

Figure 13A:
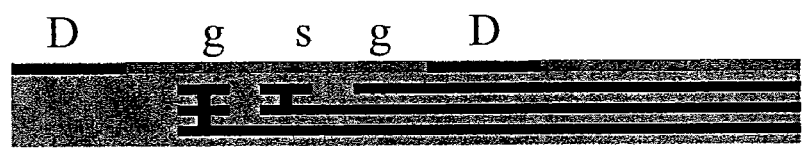
FIG. 13a illustrates a cross sectional view of a first embodiment for arranging electrodes according to the invention.
Figure 13B:
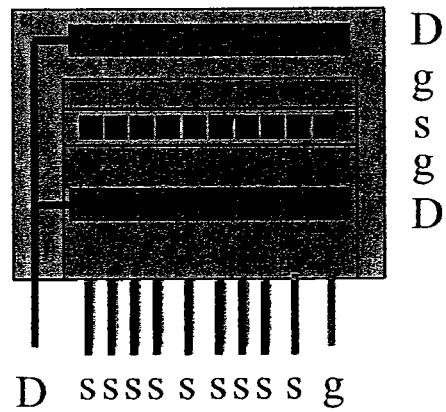
FIG. 13b illustrates a top view of a first embodiment for arranging electrodes according to the invention.

FIGS. 13a and 13b illustrate a cross-sectional view and a top view of a first embodiment of an electrode arrangement according to the invention. In this embodiment sensing electrode s is led on a conductive layer, which is between two guard layers g. this way it is possible to achieve an efficient guarding for the sensing electrode. The drive electrodes D are led on the top conductive layer.

Figure 14A:
FIG. 14a illustrates a cross sectional view of a second embodiment for arranging electrodes according to the invention.
Figure 14B:
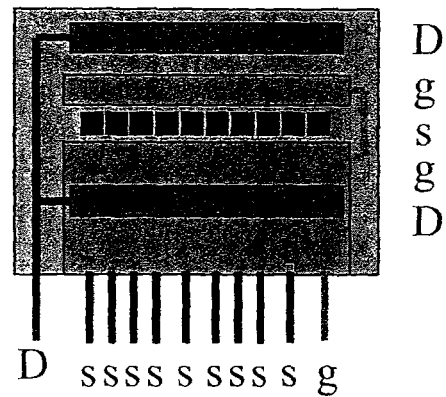
FIG. 14b illustrates a top view of a second embodiment for arranging electrodes according to the invention.

FIGS. 14a and 14b illustrate a cross-sectional view and a top view of a second embodiment of an electrode arrangement according to the invention. In this embodiment sensing electrode s is led on a conductive layer, which is between a guard layer g and a grounded EMC layer. The drive electrodes D are led on the top conductive layer.

Figure 15A:
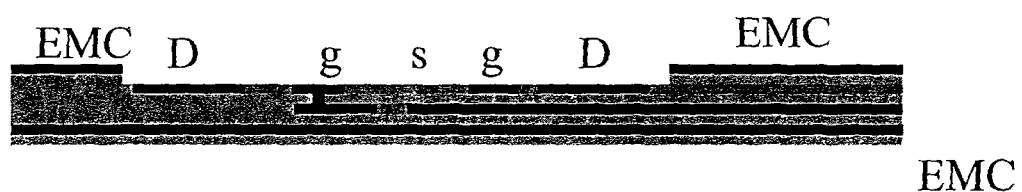
FIG. 15a illustrates a cross sectional view of a third embodiment for arranging electrodes according to the invention.
Figure 15B:
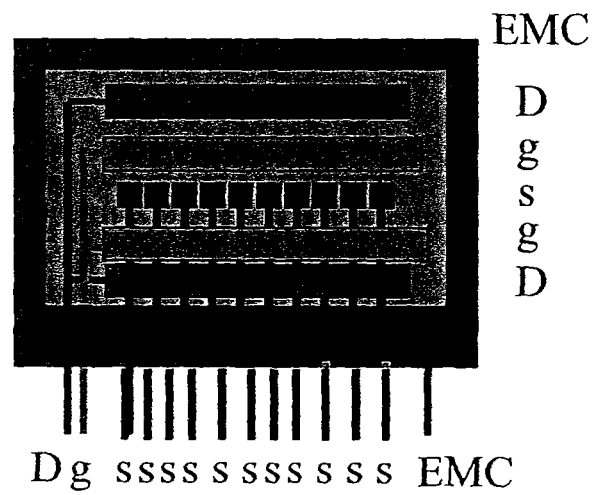
FIG. 15b illustrates a top view of a third embodiment for arranging electrodes according to the invention.

FIGS. 15a and 15b illustrate a cross-sectional view and a top view of a third embodiment of an electrode arrangement according to the invention. In this embodiment sensing electrode s is led on a conductive layer, which is between two grounded EMC layers. The guard does not have layer of its own, but it led on same layers as the sensor and drive electrodes. This is possible when the guard electrode wiring and the sensing electrode wiring are perpendicular to each other.

Figure 16A:
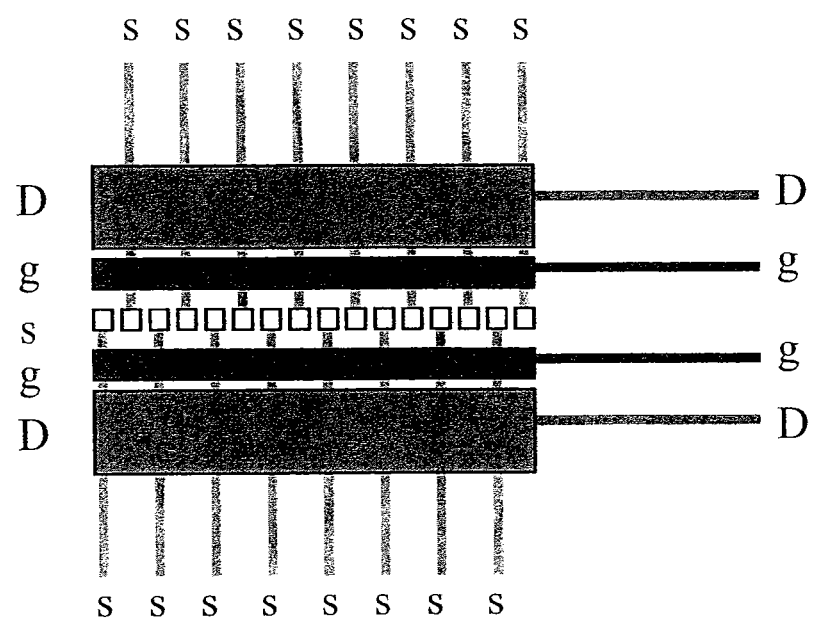
FIG. 16a illustrates a top view of a fourth embodiment for arranging electrodes according to the invention.
Figure 16B:
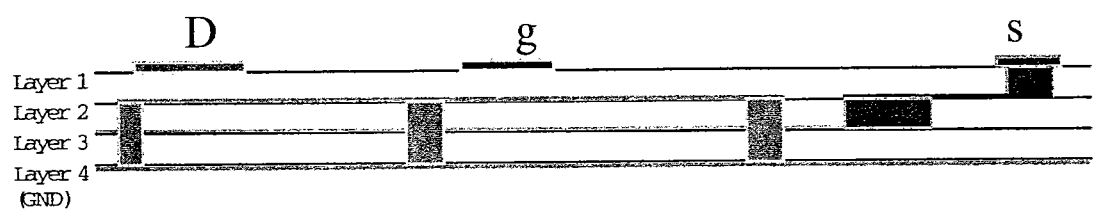
FIG. 16b illustrates a cross sectional view of a fourth embodiment for arranging electrodes according to the invention.

FIGS. 16a and 16b illustrate a top view and a cross-sectional view of a fourth embodiment of an electrode arrangement according to the invention. In this embodiment the guarding and drive electrode wiring are on the top layer, and perpendicular to the sensing electrode wiring. The sensing electrode wiring is led between two grounded EMC layers, and thus a coaxial-type shielding is achieved for the sensing electrode wiring.

In order to achieve most efficient guarding, the sensing electrodes should have an individual guard, which is individually controlled by a guard amplifier. However, since the sensing electrodes are often read in a time-multiplexed manner, it could be advantageous to use one guarding amplifier and to connect it always to the guard electrode of the sensing electrode, which is currently read. A further possibility is to use moving pixel guarding.

If the guard electrode is common to all sensing electrodes, the guard electrode can be connected e.g. to ground (passive guarding), or to an average potential of the sensing electrodes. One further possibility to reduce interference is to connect the drive electrode to the hand of the user, e.g. via the device cover.

Figure 17:
FIG. 17 illustrates a fabrication process for a circuit with a flexible substrate.
Figure 17:
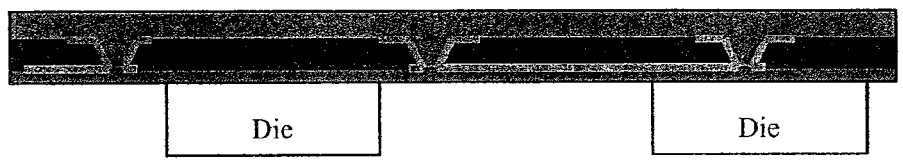
Figure 17:
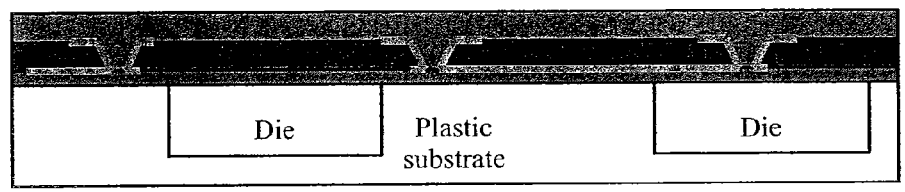
Figure 17:
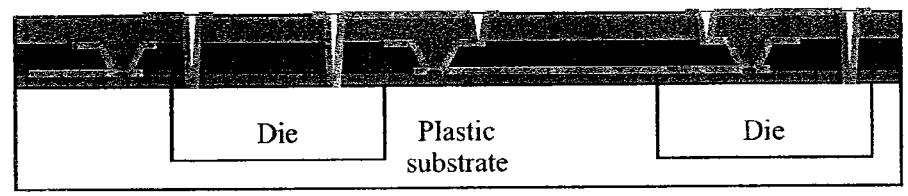
Figure 17:
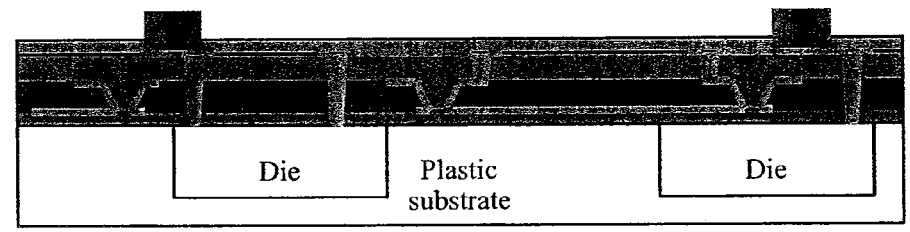

FIG. 17 illustrates an exemplary process for manufacturing an arrangement according to the invention using a flexible substrate. The Figures show a cross section of the unit to be manufactured after the concerned manufacturing phase has been executed. First in phase 11 overlay is fabricated using polyimide substrates. Also interconnects patterned with copper. On phase 12 adhesive is applied and the dies are bonded to the overlay. On phase 13 a plastic substrate is molded around the dies. On phase 14 vias are drilled and metallization is sputtered to form electrical connections. Finally, phase 15 includes passivation and deposition of solder balls for providing an external interface.

The invention has been explained above with reference to the aforementioned embodiments, and several industrial advantages of the invention have been demonstrated. It is clear that the invention is not only restricted to these embodiments, but comprises all possible embodiments within the spirit and scope of the inventive thought and the following patent claims. For example, the inventive idea of the sensor arrangement is not restricted to be used in mobile terminals, but it can be applied also in many other components and purposes. The invention is not either restricted to use of the mentioned materials. The inventive idea of inductive measurement can also be regarded as an independent invention to include implementations where there is no sensor arrangement with the present inventive use of substrate.

The invention claimed is:

1. A sensor arrangement comprising a sensor, at least one integrated signal processing circuit for the measurement of signals from the sensor, and interconnecting wiring between the sensor and the integrated circuit, the arrangement comprising a substrate, said substrate forming at least part of said interconnecting wiring and said substrate is further arranged to serve as a part of said sensor, and wherein said substrate is of a curved form to provide a surface for a finger, wherein said sensor comprises at least an optical sensor for providing said signals, at least in part, to said integrated signal processing circuit for the measurement of said signals.

2. The sensor arrangement according to claim 1, wherein said optical sensor is an optical pulse oximeter.

3. The sensor arrangement according to claim 1, wherein said sensor further comprises a circuit configured to transfer a sensed finger signal inductively to said substrate, wherein said sensor and said substrate are galvanically separated.

4. The sensor arrangement according to claim 1, wherein said sensor includes a skin contact sensor.

5. The sensor arrangement according to claim 1, wherein said optical sensor comprises a infrared light source, a infrared light detector and wherein said integrated signal processing circuit is configured to measure a detected signal from the infrared light detector indicative of absorption of infrared light from a finger.

6. The sensor arrangement according to claim 5, wherein said infrared light source and said infrared light detector are located at opposite sides of a groove of said sensor designed for sensing the finger on said substrate of said curved form.

7. The sensor arrangement according to claim 1, wherein said arrangement further comprises a temperature sensor for measuring ambient temperature.

8. The sensor arrangement according to claim 1, wherein said arrangement further comprises a humidity sensor for sensing ambient humidity.

9. The sensor arrangement according to claim 1, wherein said arrangement further comprises a pressure sensor.

10. The sensor arrangement according to claim 1, wherein said arrangement further comprises a skin contact sensor.

11. The sensor arrangement according to claim 1, wherein said arrangement further comprises at least one sensor part of said sensor fixed on the substrate.

12. The sensor arrangement according to claim 1, wherein said sensor comprises a biometric sensor.

13. A mobile terminal, comprising a sensor arrangement according to claim 1.

14. The mobile terminal of claim 13, wherein at least part of the sensor arrangement is encapsulated by a cover of the mobile terminal.

15. The mobile terminal of claim 13, wherein at least part of the sensor arrangement is molded in a cover of the mobile terminal.

16. The mobile terminal according to claim 13, wherein said surface for said finger in said curved form of said substrate is flexible.

17. The mobile terminal according to claim 13, wherein said substrate forming at least part of said interconnecting wiring is flexible.

18. The sensor arrangement according to claim 1, wherein said substrate is flexible, at least in part.

19. The mobile terminal according to claim 13, wherein at least part of the sensor arrangement is on a cover of the mobile terminal.

* * * * *